US006342213B1

(12) United States Patent
Barley et al.

(10) Patent No.: US 6,342,213 B1
(45) Date of Patent: Jan. 29, 2002

(54) METHODS FOR TREATING NON-SUTURABLE WOUNDS BY USE OF CYANOACRYLATE ADHESIVES

(75) Inventors: Leonard V. Barley; Linda M. Barley; J. Royce Renfrow, all of Colorado Springs; Patrick J. Tighe, Littleton, all of CO (US)

(73) Assignee: MedLogic Global Corporation, Colorado Springs, CO (US)

(*) Notice: Subject to any disclaimer, the term of this patent is extended or adjusted under 35 U.S.C. 154(b) by 0 days.

(21) Appl. No.: 08/231,638

(22) Filed: Apr. 22, 1994

Related U.S. Application Data

(63) Continuation-in-part of application No. 08/133,190, filed on Oct. 19, 1993, now abandoned, which is a continuation-in-part of application No. 07/895,589, filed on May 9, 1992, now abandoned.

(51) Int. Cl.[7] .............................................. A61K 31/78
(52) U.S. Cl. .............................. 424/78.35; 424/78.02; 424/78.05; 424/78.06; 424/78.07; 424/78.27; 424/407; 523/111
(58) Field of Search ........................... 424/78.35, 78.02, 424/78.08, 443, 78.05, 78.06, 78.27, 445; 523/111; 602/42, 43, 52, 54, 904

(56) References Cited

U.S. PATENT DOCUMENTS

| | | | |
|---|---|---|---|
| 2,804,073 A | 8/1957 | Galliene et al. | 128/156 |
| 3,527,224 A | 9/1970 | Rabinowitz | 526/297 |
| 3,591,676 A | 7/1971 | Hawkins et al. | 424/78.06 |
| 3,667,472 A | 6/1972 | Halpern | 128/334 R |
| 3,722,599 A | 3/1973 | Robertson et al. | |
| 3,995,641 A | 12/1976 | Kroenthal et al. | 558/400 |
| 4,035,334 A | 7/1977 | Davydov et al. | 424/78.06 |
| 4,444,933 A | 4/1984 | Columbus et al. | 524/292 |
| 4,650,826 A | 3/1987 | Waniczek et al. | 524/292 |
| 4,958,748 A | 9/1990 | Otake | 222/108 |
| 5,306,490 A * | 4/1994 | Barley, Jr. | 424/38.35 |
| 5,514,372 A * | 5/1996 | Leung et al. | 424/78.35 |

OTHER PUBLICATIONS

Lehman, Ralph A.W. et al., "Toxicity of Alkyl 2–Cyanoacrylate: Bacterial Growth", pp 447–450, Sep. 1966, Archives of Surgery, vol. 93.
Leonard, Fred et al., "Synthesis and Degradation of Poly-(alkyl–a–Cyanoacrylate)", pp 259–272, 1966, Journal of Applied Polymer Science, vol. 10.
Makady, F.M. et al., "Effect of tissue adhesives and suture patterns on experimentally induced teat lacerations in lactating dairy cattle", pp 1932–1934, Jun. 1991, JAVMA, Reports of Original Studies, vol. 198, No. 11.
Matsumoto, Teruo, "Becteriology and Wound Healing", pp 106–113, 1972, Chapter 3 in Tissue Adhesives in Surgery.

Matsumoto, Teruo, "Clinical Considerations and Appplications of Bucrylate Tissue Advesive", pp 226–237, 1972, Tissue Adhesives in Surgery, Chap. 1, Sec. III.
Matsumoto, Teruo, "Reactions of the Organism to Acrylate–Adhesives", pp 436–444, 1972, Tissue Adhesives in Surgery.
Matsumoto, Teruo et al., "Tissue Adhesive and Wound Healing", pp 266–271, Mar. 1969, Archives of Surgery, vol. 98.
Mizrahi, S. et al., "Use of Tissue Adhesives in the Repair of Lacerations in Children", pp 312–313, Apr. 1988, Journal of Pediatric Surgery, vol. 23, No. 4.
Morton, R.J. et al., "The Use of Histoacryl Tissue Adhesive for the Primary Closure of Scalp Wounds", pp 110–112, 1988, Archives of Emergency Medicine, vol. 5.
Ousterhout, D.K. et al., "Cultaneous Absorption of n–Alkyl–a–Cyanocrylate", pp 157–163, 1968, Journal of Biomedical Materials Research, vol. 2.
Pepper, D.C., "Kinetics and Mechanism of Zwitterionic Polymerization of Alkyl Cyanocrylate", pp 629–637, 1980, Polymer Journal, vol. 12, No. 9.
Pepper, David Charles et al., "Kinetics of Polymerization of Alkyl Cyanoacrylate by Tertiary Amines and Phosphines", pp 395–410, 1983, Makromol. Chem., vol. 184.
Ronis, Max L. et al., "Review of Cyanoacylate Tissue Glues with Emphasis of Their Otorhinolaryngological Applications", pp 210–213, Feb. 1984, Laryngoscope., vol. 94.
Saches, Michael Evan., "Enbucrylate as Cartilage Adhesive in Augmentation Rhinoplasty", pp 389–393, Jun. 1985, Archives of Otolaryngology, vol. 111.
Toriumi, Dean M. et al., "Histotoxicity of Cyanoacrylate Tissue Adhesives: A Comparative Study", pp 546–550, Jun. 1990, Archives of Otolaryngology Head and Neck Surgery, vol. 116.
Tseng, Yin–Chao et al., "Modification of Synthesis and Investigation of Properties for 2–cyanoacrylate", pp 73–79, Jan. 1990, Biomaterials, vol. 11.
Vinters, H.V. et al., "The Histotoxicity of Cyanoacrylate: A Selective Review", pp 279–291, 1985, Neuroradiology, vol. 27.
Watson, David P., "Use of Cyanoacrylate Tissue Adhesive for Closing Facial Lacerations in Children", p 1014, Oct. 1989, British Medical Journal, vol. 299.
Akers, William A., "Treating Friction Blisters With Alkyl–α–Cyanoacrylates", Arch Dermatol, vol. 107, 544–547, Apr. 1973.
Bhaskar, Surindar N. et al., "Healing of Skin Wounds with Butyl Cyanoacrylate", pp 294–297, 1969, Journal of Dental Research, vol. 48, No. 2.

(List continued on next page.)

Primary Examiner—Neil S. Levy
(74) Attorney, Agent, or Firm—Burns, Doane, Swecker & Mathis LLP

(57) ABSTRACT

A cyanoacrylate adhesive is applied to non-suturable, non-sterile wound surfaces to protect and/or treat such surfaces, to promote wound healing and to retard infection of the wound.

5 Claims, No Drawings

U.S. PATENT DOCUMENTS

Dalvi, A. et al., "Non–suture Closure of Wound Using Cyanocrylate", 97–100, 1986, Journal of Postgraduate Medicine, vol. 32, No. 2.

Eiferman, Richard A. et al., "Antibacterial Effects of Cyanoacrylate Glue", pp 958–960, Jun. 1983, Archives of Ophthalmology, vol. 101.

Ellis, David A.F. et al., "The Ideal Tissue Adhesive in Facial Plastic and Reconstructive Surgery", pp 68–72, 1990, The Journal of Otolaryngology, vol. 19, No. 1.

Fung, Ramona Q. et al., "Use of Butyl–2–Cyanoacrylate in Rabbit Auricular Cartilage", pp 459–464, Jul. 1985, Archives of Otolaryngology, vol. 111.

Galil, K.A. et al., "The Healing of Hamster Skin Ulcers Treated with N–butyl–2–cyanoacrylate(Histoacryl blue)", pp 601–607, 1984, Journal of Biomedical Materials Research, vol. 18.

Harper, Marion C., "Stabilization of Osteochondral Fragments Using Limited Placement of Cyanoacrylate in Rabbits", pp 272–276, Jun. 1988, Clinical Orthopaedics and Related Research 231.

Kamer, Frank M. et al., "Histoacryl: Its Use in Aesthetic Facial Pastic Surgery", pp 193–197, Feb. 1989, Archives of Otolaryngology Head and Neck Surgery, vol. 115.

Kosko, Paul I. "Upper Lid Blepharoplasty: Skin Closure Achieved with Butyl–2–Cyanoacrylate", pp 424–425, Jun. 1981, Ophthalmic Surgery, vol. 12.

* cited by examiner

METHODS FOR TREATING NON-SUTURABLE WOUNDS BY USE OF CYANOACRYLATE ADHESIVES

CROSS-REFERENCE TO RELATED APPLICATIONS

This application is a continuation-in-part of U.S. patent application Ser. No. 08/133,199 filed Oct. 19, 1993 (derived from International Application Ser. No. PCT/US93/05487), now abandoned, which is a continuation-in-part of U.S. patent application Ser. No. 07/895,589, filed Jun. 9, 1992 also now abandoned, both of which applications are incorporated herein by reference in their entirety.

BACKGROUND OF THE INVENTION

1. Field of the Invention

This invention is directed to methods for treating non-suturable wounds by using cyanoacrylate adhesives. The cyanoacrylate adhesive to be used can be stored in dispensers for single or repeated/inter-mittent use.

2. State of the Art

Cyanoacrylate adhesives have been suggested for a variety of adhesive purposes including glues and surgical adhesives. In particular, cyanoacrylates of formula I:

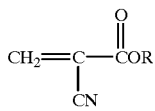

wherein R is an alkyl or other suitable substituent are disclosed in U.S. Pat. Nos. 3,527,224; 3,591,676; 3,667,472; 3,995,641; 4,035,334; and 4,650,826. Typically, when used as an adhesive for living tissues, the R substituent is alkyl of from 2 to 8 carbon atoms and most often is butyl (e.g., n-butyl).

The suggested medical uses for cyanoacrylate adhesives include surgical environments wherein the cyanoacrylate adhesive is utilized, e.g., as an alternative to sutures or as a hemostat and, as such, are necessarily employed in a sterile environment. See, for example, Halpern, U.S. Pat. No. 3,667,472, and Robertson, et al., U.S. Pat. No. 3,722,599. In such surgical environments, the cyanoacrylate adhesive is applied to the soft tissue under sterile conditions and, in the presence of water or protein found in soft tissue, the adhesive bonds to the tissue as well as polymerizes which, in the case of adhesive sutures, joins the separated sections of soft tissue together.

Contrarily, most small wounds are neither treated in a surgical setting nor in a sterile environment. In a typical home setting, small wounds are generally cleaned and are either left exposed (generally if not bleeding) or are covered with a bandage (generally the case where minor bleeding occurs or where there is irritation). In either case, the wound is usually left to heal on its own over time with the accompanying discomfort during this period.

In any event, the art teaches against the use of alkyl cyanoacrylates on human skin tissue where it will be absorbed internally because of the lack of suitable low toxicity and/or adequate resorption/absorption properties for these cyanoacrylates. See, for example, Robertson, et al., U.S. Pat. No. 3,722,599. Specifically, it has been reported that, when used as suture supplements or internally, polymeric residue of higher homologs of alkyl cyanoacrylate (e.g., n-butyl cyanoacrylate) has been observed by histological examination of the site of application as much as 12 months after application. Apparently, the cyanoacrylate polymeric residue is encased internally and, due to low biological absorption/resorption properties, remains at the site of application for prolonged periods of time. Such poor absorption/resorption properties are contra-indicative for their use as tissue adhesives.

SUMMARY OF THE INVENTION

This invention is drawn to methods for treating and/or protecting small superficial wounds by the application of alkyl cyanoacrylate adhesive to the surface of such wounds. Such small superficial wounds are characterized as superficial cuts or abrasions not penetrating through the dermal layer of the skin surface to the subcutaneous layer or tissue.

This invention is based, in part, on the discovery that application of cyanoacrylate adhesive to such small superficial wounds will not result in the undesirable prolonged internalization of polymeric adhesive. Without being limited to any theory, Applicants believe that such internalization of the polymeric residue does not occur because any polymeric residue entrapped within the epidermal and/or dermal layer will be shed as part of the normal shedding of these layers.

Moreover, contrary to typical prior art application methods, Applicants have found that by limiting application to such superficial cuts and abrasions, the cyanoacrylate adhesive can be applied under non-sterile conditions typically employed in consumer usage.

The methods of this invention involve applying a cyanoacrylate adhesive, particularly, n-butyl cyanoacrylate adhesive, onto the wound under non-sterile conditions and allowing the adhesive to polymerize.

In the case of cuts, the cyanoacrylate adhesive is generally applied between the separated skin defining the cut as well as over the cut. The cyanoacrylate adhesive is then allowed to polymerize so as to both bind the separated skin sections and form a polymer layer over the cut. In addition to serving as a protective layer, the polymer layer also serves to promote healing and to retard infection of the cut.

In the case of abrasions, the cyanoacrylate adhesive is generally applied over the abrasion. The cyanoacrylate adhesive is allowed to polymerize so as to form a polymer layer over the abrasion. The polymer layer serves to act as a protective layer which prevents further aggravation to the abrasion while also promoting healing and retarding infection of the abrasion.

Accordingly, in one of its method aspects, this invention is directed to a method for treating and/or protecting non-suturable superficial wounds which comprises:

applying to the surface of a non-suturable wound, in a non-sterile environment, a sufficient amount of a cyanoacrylate adhesive so as to cover the entire wound area wherein the wound is characterized as superficial cuts and/or abrasions which do not penetrate through the dermal layer of the skin surface to the subcutaneous layer; and polymerizing the cyanoacrylate adhesive so as to join separated skin sections and/or to form an adhesive coating which adheres to the area where the adhesive was applied, wherein the cyanoacrylate, in monomeric form, is represented by formula I:

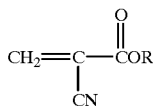

where R is alkyl of 2 to 10 carbon atoms.

Preferably R is alkyl of from 2 to 8 carbon atoms and more preferably alkyl of from 4 to 8 carbon atoms. Most preferably, R is either n-butyl or octyl.

In another of its method aspects, this invention is directed to a method for treating and/or protecting superficial non-suturable cuts which method comprises:

applying to the surface of a non-suturable cut in a non-sterile environment, a sufficient amount of n-butyl cyanoacrylate adhesive to cover the entire cut area wherein said cut is characterized as a superficial cut which does not penetrate through the dermal layer of the skin surface to the subcutaneous layer; and polymerizing the cyanoacrylate adhesive so as to join separated skin sections and to form an adhesive coating which adheres to the area where the adhesive was applied wherein, in monomeric form, the n-butyl cyanoacrylate adhesive is represented by the formula:

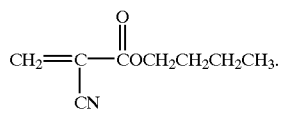

In a preferred embodiment, the cyanoacrylate is applied at least about 0.02 milliliter (ml), more preferably from about 0.02 to about 0.2 ml, and still more preferably from about 0.02 to about 0.1 ml, of cyanoacrylate adhesive per square centimeter of skin which is to be covered.

In another preferred embodiment, the cyanoacrylate adhesive to be applied to the skin has a viscosity of from about 2 to about 3000 centipoise at 20° C. More preferably, the cyanoacrylate adhesive is in monomeric form and has a viscosity of from about 2 to about 100 centipoise at 20° C.

As used herein, the following terms have the following meanings:

the term "cyanoacrylate adhesive" refers to adhesive formulations based on cyanoacrylate monomers of formula I:

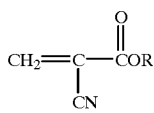

where R is selected from the group consisting of alkyl of 2 to 10 carbon atoms.

Preferably, R is an alkyl group of from 2–8 carbon atoms including ethyl, n-propyl, iso-propyl, n-butyl, iso-butyl, sec-butyl, n-pentyl, iso-pentyl, n-hexyl, iso-hexyl, 2-ethyl-hexyl, n-heptyl, and octyl. More preferably, R is butyl or octyl and most preferably, R is n-butyl.

These cyanoacrylate adhesives are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

Preferred cyanoacrylate adhesives for use in this invention are n-butyl-2-cyanoacrylate and octyl-2-cyanoacrylate.

The cyanoacrylate adhesives described herein rapidly polymerize in the presence of water vapor or tissue protein, and the n-butyl-cyanoacrylate is capable of bonding human skin tissue without causing histoxicity or cytotoxicity.

The term "non-suturable or small wounds" means superficial cuts and abrasions characterized as superficial cuts and/or abrasions which do not penetrate through the dermal layer of the skin surface to the subcutaneous layer. Such superficial wounds include cuts where the skin is separated and can be joined together, as well as abrasions such as "nicks" or "scrapes" where the skin is removed. However, non-suturable wounds do not include puncture wounds.

In view of the above, non-suturable wounds as defined herein include common cuts and scratches which rarely need medical attention unless located in a sensitive area or unless secondary infection occurs. As opposed to the edges of suturable wounds which can be widely separated, the edges of non-suturable wounds can easily be opposed or brought together. One particular example of a non-suturable wound treatable by the methods of this invention is skin tearing adjacent the site of a catheter implant.

DETAILED DESCRIPTION OF THE PREFERRED EMBODIMENTS

This invention relates to methods for treating and/or protecting non-suturable superficial wound surfaces with cyanoacrylate adhesives in an every day, typical non-sterile environment.

The cyanoacrylate adhesive to-be-applied to the superficial wound surface can be monomeric or partially polymeric. In general, partially polymerized cyanoacrylate adhesives are liquid polymers having a higher viscosity than that of the corresponding monomer and, therefore, are better suited for those applications which are intended to be specific for a particular skin area. In other words, less viscous materials are more likely to "run" (i.e., flow) into areas where application was not intended.

The cyanoacrylate adhesives used herein preferably have a viscosity of from about 2 to about 3000 centipoise and more preferably from about 2 to about 100 centipoise at 20° C. It is contemplated, however, that pastes and gels having viscosities of up to 50,000 centipoise at 20° C. can also be employed and will make for easier skin application.

The specific viscosity of the formulation depends, in part, on the amount and degree of partially polymerized cyanoacrylate adhesive employed as well as additives which are employed in the formulation to enhance or decrease viscosity. Such factors are readily ascertainable by the skilled artisan. For example, methods for preparing partially polymerized cyanoacrylate adhesives are disclosed, for example, by Rabinowitz, U.S. Pat. No. 3,527,224 which is incorporated herein by reference in its entirety. Additives which can be incorporated into the formulation to enhance its viscosity include polymers such as polymethyl methacrylate (PMMA) and polymerized cyanoacrylate adhesives as disclosed in U.S. Pat. Nos. 3,654,239 and 4,038,345 both of which are incorporated herein by reference in their entirety.

Monomeric forms of cyanoacrylate adhesives are often preferred where application is to be made to a large surface area. This preference results from the fact that these forms are less viscous and, accordingly, will permit more facile large surface area application. Mixtures of monomeric forms of cyanoacrylate adhesive and partially polymerized forms of cyanoacrylate adhesive can also be used to prepare a formulation having intermediate viscosities.

For purposes of this invention, monomeric or partially polymerized n-butyl-2-cyanoacrylate is a particularly preferred adhesive and is capable of effectively bonding human skin tissue without causing histoxicity or cytotoxicity.

Upon contact with skin moisture and tissue protein, the cyanoacrylate adhesives will polymerize or, in the case of partially polymerized cyanoacrylate adhesives, will further polymerize, at ambient conditions (skin temperature) over about 10 seconds to 60 seconds to provide a solid layer which forms over and strongly adheres to the surface of the skin, thus providing a protective layer to the wound area.

The adhesive is applied to provide an effectively thick coating over the surface of the superficial wound. Because the to-be-treated wound is superficial and does not extend beyond the dermal layer, any polymeric residues diffusing into or forming in the wound will be naturally extruded from the skin. Generally, the adhesive provides an adhesive film coating over the wound area which when set is satisfactorily flexible and adherent to the tissue without premature peeling or cracking. Preferably, the adhesive coating has a thickness of less than about 0.5 millimeter (mm), and more preferably the coating has a thickness of less than about 0.3 mm. In a particularly preferred embodiment, the thickness of the adhesive coating is from about 0.1 millimeter to about 0.5 millimeter and even more preferably from about 0.1 millimeter to about 0.3 millimeter.

Adhesive coatings of such thicknesses form a physical barrier layer over superficial wounds which coatings provide protection for the wound in the same manner as a conventional bandage, e.g., Band-Aid™ brand bandages. Specifically, the cyanoacrylate adhesive coating provides an airtight, waterproof seal around the wound which does not need to be replaced when the wound gets wet. Once applied, the coating prevents bacterial and contaminant entry into the wound, thus reducing the rate of secondary infection. Generally, the adhesive coating does not limit dexterity and promotes faster wound healing.

Additionally, unlike conventional bandages, the adhesive coating of this invention naturally sloughs off the skin within 2–3 days after application and, accordingly, avoids the discomfort associated with removal of conventional bandages from the skin. However, if early removal of this polymeric coating is desired, such can be achieved by use of solvents such as acetone.

The adhesive coating can be formed by applying at least about 0.02 ml of cyanoacrylate adhesive per square centimeter of skin, more preferably from about 0.02 to about 0.2 ml, and still more preferably from about 0.02 to about 0.1 ml, of cyanoacrylate adhesive per square centimeter of skin and yet more preferably from about 0.02 to about 0.05 ml of cyanoacrylate adhesive per square centimeter of skin.

FORMULATIONS

The cyanoacrylate adhesive formulations employed herein generally comprise monomeric and/or partially polymerized compounds of formula I described above and are sometimes referred to herein as simply cyanoacrylate adhesives. These formulations are liquid in nature and, upon contact with surface skin proteins and moisture, will polymerize to provide a solid film or layer over the skin surface.

The formulations may additionally contain one or more optional additives such as colorants, plasticizers, perfumes, anti-diffusion agents, modifying agents and stabilizers. In practice, each of these optional additives should be both miscible and compatible with the cyanoacrylate adhesive. Compatible additives are those that do not prevent the use of the cyanoacrylate adhesives in the manner described herein.

In general, colorants are added so that the polymerized film will contain a discrete and discernable color. Perfumes are added to provide a pleasant smell to the formulation. Stabilizers, such as sulfur dioxide, are added to retard in situ polymerization in containers during storage. Plasticizers, such as dioctylphthalate or tri (p-cresyl)phosphate, are added in order to enhance the flexibility of the resulting polymer layer. Each of these additives is conventional. For example, suitable stabilizers are disclosed in U.S. Pat. No. 4,650,826 and suitable plasticizers are disclosed in U.S. Pat. Nos. 2,784,127 and 4,444,933 the disclosures of all of these patents being incorporated herein by reference in their entirety.

The amount of each of these optional additives employed in the cyanoacrylate adhesive is an amount necessary to achieve the desired effect.

The formulation is generally stored in an applicator for use in a single dose application or for use in repeated applications. Single dose applicators include those having breakable or removable seals that prevent moisture, including atmospheric moisture, from contacting the formulation and causing in situ polymerization.

For repeated and intermittent usage, minimal exposure to atmospheric moisture is required. This can be achieved by devices having very narrow outlets and low initial dead space. One applicator for such repeated intermittent use is described in U.S. Pat. No. 4,958,748 which is incorporated herein by reference in its entirety.

Another applicator comprises a conventional spray applicator wherein the cyanoacrylate adhesive is sprayed onto the surface skin area which includes the superficial wound. The spray rate of the applicator can be controlled so that application of a metered quantity of adhesive per unit area of skin surface over a set period of time is controlled.

Still another applicator comprises a brush or solid paddle applicator wherein the cyanoacrylate adhesive is "painted" onto the surface skin area containing the superficial wound.

A preferred applicator for repeated and intermittent usage is an applicator suitable for the non-sterile storage and metered dispersement of a cyanoacrylate adhesive after opening of the applicator wherein the applicator is characterized as having a resealable opening of no more than about 0.008 square inches (0.0516 square centimeters) so as to permit the metered dispersement of the adhesive from the applicator and which is capable of multiple administrations of the adhesive and is further characterized as having resealing means such as a cap which either tightly mates with the applicator or which screws onto the applicator.

Preferably, the opening of the applicator is about 0.0016 to about 0.003 square inches (about 0.0103 to about 0.0194 square centimeters).

In another preferred embodiment, the walls of the applicator are made of a pliable material, so that upon application of pressure onto the walls, the walls depress sufficiently to force the adhesive contained in the applicator through the opening. Preferably, the applicator is manufactured with its opening covered by a metal foil or other similar construction which closes this opening until the device is ready for use. The opening is then reinstated by use of a pin or similar device which punctures the covering.

In applicators suitable for repeated intermittent uses, the cyanoacrylate adhesive is stored at ambient conditions and is selected to be bacteriostatic. See, for example, Rabinowitz et al., U.S. Pat. No. 3,527,224. When the selected adhesive is bacteriostatic, prolonged storage at ambient conditions is without regard to the sterility of the formulation because there is no adverse buildup of bacteria during storage.

METHODOLOGY

The above-described formulations are applied to a wound area under conditions suitable for polymerizing the adhesive so as to form a protective coating. In general, the wound is usually first cleaned (soap/water and optionally a disinfectant), and then sufficient amounts of cyanoacrylate adhesive are employed to cover or encase the entire scrape, scratch or nick area and is preferably extended by at least about 1 centimeter beyond the wound. No other sterilization methods are required as the methods of this invention are readily practiced in a non-sterile environment.

For cuts, an amount sufficient to join the opposing skin edges is applied, and optionally a sufficient amount is applied to also encase the entire cut area. For scrapes, a sufficient amount is applied to encase the entire wound area.

In either case, the adhesive polymer coating should preferably be maintained in a unbroken manner over the entire wound area. This can be assured by careful application of the adhesive onto the skin/wound. Additionally, the use of a plasticizer will facilitate the maintenance of the polymer coating in an unbroken manner. However, to further ensure that the polymer coating is maintained unbroken, after the initial layer of adhesive has cured to provide for an adhesive polymer coating, a second, preferably thinner, layer is applied over the adhesive polymer coating. Additional amounts of cyanoacrylate adhesive can be applied as needed to maintain an unbroken coating covering over the wound areas.

When the adhesive is applied to cover or encase the wound area, sufficient cyanoacrylate adhesive is preferably employed to form a coating of less than about 0.5 mm thick and more preferably at least about 0.1 mm thick. Such coatings are formed by applying at least about 0.02 ml of cyanoacrylate adhesive per square centimeter of skin surface area.

The amount of cyanoacrylate adhesive applied onto the skin surface area can be controlled by the amount of adhesive packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is particularly advantageous because it dispenses the adhesive in a controlled drop wise manner. Other methods for the controlled dispersement of the cyanoacrylate adhesive are as described above including, by way of example, a conventional spray applicator, a brush or solid paddle applicator, and the like.

Upon application of the cyanoacrylate adhesive, the surface skin moisture, tissue protein, and temperature are sufficient to initiate polymerization of the adhesive upon application. Thereafter, the skin surface is maintained under suitable conditions to allow polymerization to proceed to formation of an adhesive coating.

In general, the particular length of time required for polymerization will vary depending on factors such as the amount of adhesive applied, the temperature of the skin, the moisture content of the skin, the surface area of the wound, and the like. However, in a preferred embodiment, polymerization is generally complete within about 10 seconds to about 60 seconds while the skin is maintained at ambient conditions. During this period, the person to whom application of the cyanoacrylate adhesive has been made merely allows the adhesive to form a coating while minimizing any action to prevent the adhesive from being dislodged from that portion of the skin where it was applied or to adhere to unintended objects. Excess adhesive polymer can be removed with acetone (nail polish remover) which can be readily conducted except in the case where the adhesive polymer binds to a sensitive skin part (e.g., eye lids) where it should be removed by a health care professional. After the adhesive coating has formed, the coating strongly adheres to the skin, is flexible and waterproof, thereby protecting the wound area and promoting healing.

It is important to note that the adhesive coating of the invention can be applied in a non-sterile environment to a non-sterile surface. This is directly contrary to the use of cyanoacrylates as surgical adhesives which requires one-time use in a sterile environment. The invention provides for storage of the adhesive in a dispenser for repeated intermittent uses in a non-sterile environment.

In general, the coating will adhere to the skin for a period of about 2–3 days after which time it sloughs off. Additional applications can be made if desired.

The coating protects non-suturable wounds because the adhesive forms a polymer coating which extends over the entire surface of the wound to protect the wound in much the way a bandage does while, in the case of cuts, also joins together the separated skin surfaces. Because the coating is waterproof, the patient is not prevented from bathing and other activities involving exposure to water during the period the adhesive layer protects the wound.

One particular example of a non-suturable wound treatable by the methods of this invention is skin tearing adjacent the site of a catheter implant. Specifically, it is common after catheter implantation to have the skin adjacent the catheter to tear, partially due to catheter movement relative to the site of catheter implantation due to the patient's muscle contractions, etc. Such tears are typically non-suturable wounds and can become the site of infection and are prone to further tearing. Moreover, as the skin tears adjacent a catheter implant, it becomes difficult to maintain the catheter in the implant site. Heretofore, there were no acceptable methods to treat such tearing and potentially inadvertent catheter removal other than to reinsert the catheter at another site.

The methods of this invention now provide for a method to treat such tearing without removal of the catheter. Specifically, in this particular aspect of the methods of this invention, the cyanoacrylate adhesive is applied onto these tears and then polymerized as described generally above. This results in joining the separated skin sections of the tear which protects the tear and retards further tearing thereof.

This method can also be employed prophylactically by applying the cyanoacrylate adhesive to the skin areas adjacent the catheter prior to actual skin tearing. In this regard, application is generally made in the manner and amounts described above and is preferably applied to the skin area approximately 1 centimeter and preferably about 0.5 centimeter in diameter around the catheter implant.

Accordingly, this aspect of the present invention is directed to a method for retarding skin tearing adjacent a catheter implant which method comprises:

applying a sufficient amount of a cyanoacrylate adhesive so as to cover an untorn skin area adjacent a catheter implant; and polymerizing the cyanoacrylate adhesive so as to form a polymer film over the skin area which film adheres to the skin area where the adhesive was applied, wherein the cyanoacrylate adhesive, in monomeric form, is represented by formula I as described above.

In the above prophylactic methods, the polymer film or coating is preferably less than about 0.5 millimeter in thickness and more preferably from about 0.1 to about 0.5 millimeter in thickness and still more preferably, from about 0.1 to about 0.3 millimeter in thickness.

Whether employed prophylactically or to treat existing tears, care should be taken during application of the cyanoacrylate adhesive to the skin areas adjacent catheter implantation to ensure against penetration of the adhesive into the skin puncture defined by the catheter so as to avoid skin irritation. One method for avoiding such penetration of the adhesive is to employ a viscous cyanoacrylate adhesive formulation preferably having a viscosity of from about 40 to about 100 centipoise at 20° C. Such viscous formulations tend to remain at the site of application and not run into the puncture wound. Moreover, a colorant can be incorporated into the cyanoacrylate adhesive composition to readily discern where the adhesive has been applied.

Still another particular example of a non-suturable wound treatable by the methods of this invention is the superficial skin tearing remaining after suture removal. Typically, in the case of suturable wounds (e.g., surgical wounds), the separated skin sections are joined by either sutures or by staples (collectively "sutures"), and the wound typically heals outward. That is to say that the internal sections of the wound heal first with subsequent healing outward to the skin surface. Accordingly, when the sutures are removed, the remaining wound is typically a superficial non-suturable wound because the non-healed portions of the original wound typically extend only to the dermal layer of the skin. In this regard, application of the cyanoacrylate adhesive to these wounds after suture removal as per the methods described herein provides an effective method to treat these wounds. Additionally, when the adhesive is applied to form an adhesive coating over the wound, the resulting coating is waterproof and flexible thereby allowing the patient significant freedom in bathing, swimming, etc. as compared to current practice after suture removal where the patient is instructed to minimize water contact with the wound for several days.

The following examples illustrates certain embodiments of the invention but is not meant to limit the scope of the claims in any way.

EXAMPLES

Example 1

A cyanoacrylate adhesive formulation was prepared in monomeric form using n-butyl α-cyano-acrylate. The formulation was placed into the dispensing device described by Otake, U.S. Pat. No. 4,958,748.

One drop of such a formulation is placed drop wise onto the skin of a finger having a paper cut of about 0.05 centimeter in depth and about 3 centimeters in length. At this depth, the cut does not penetrate through the dermal layer. About 30 seconds is allowed for polymerization of the adhesive. At which time, the separated skin areas defining the cut are both joined and encased by a polymer coating.

Example 2

A cyanoacrylate adhesive formulation is prepared in monomeric form using n-butyl α-cyano-acrylate and which contains a colorant to readily ascertain where the formulation has been applied, 20 weight percent of dioctyl phthalate which acts as a plasticizer to enhance the flexibility of the resulting polymer composition, and 200 parts per million (ppm) of sulfur dioxide which acts as a stabilizer. The formulation is placed into the dispensing device described by Otake, U.S. Pat. No. 4,958,748.

One drop of such a formulation is placed drop wise onto the skin of a finger having a paper cut of about 0.05 centimeter in depth and about 3 centimeters in length. At this depth, the cut does not penetrate through the dermal layer. About 30 seconds is allowed for polymerization of the adhesive. At which time, the separated skin areas defining the cut are both joined and encased by a polymer coating.

From the foregoing description, various modifications and changes in the composition and method will occur to those skilled in the art. All such modifications coming within the scope of the appended claims are intended to be included therein.

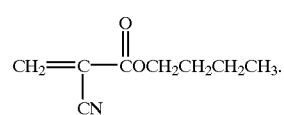

What is claimed is:

1. A method for treating and/or protecting non-suturable superficial wounds which comprises:

applying to the surface of a non-suturable wound, in a non-sterile environment, a sufficient amount of a cyanoacrylate adhesive so as to cover the entire wound area wherein the wound is characterized as superficial cuts and/or abrasions which do not penetrate through the dermal layer of the skin surface to the subcutaneous layer; and polymerizing the cyanoacrylate adhesive so as to join separated skin sections and/or to form an adhesive coating which adheres to the area where the adhesive was applied, wherein the cyanoacrylate, in monomeric form, is represented by formula I:

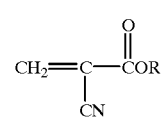

I where R is alkyl of 2 to 10 carbon atoms.

2. A method according to claim 1 wherein R is alkyl of from 2 to 8 carbon atoms.

3. A method according to claim 2 wherein R is butyl or octyl.

4. A method according to claim 3 wherein R is n-butyl.

5. A method for treating and/or protecting superficial non-suturable cuts which method comprises:

applying to the surface of a non-suturable cut in a non-sterile environment, a sufficient amount of n-butyl cyanoacrylate adhesive to cover the entire cut area wherein said cut is characterized as a superficial cut which does not penetrate through the dermal layer of the skin to the subcutaneous layer; and polymerizing the cyanoacrylate adhesive so as to join separated skin sections and to form an adhesive coating which adheres to the area where the adhesive was applied wherein, in monomeric form, the n-butyl cyanoacrylate adhesive is represented by the formula: